United States Patent [19]

Domke et al.

[11] Patent Number: 5,376,360

[45] Date of Patent: Dec. 27, 1994

[54] BAKING SODA TOOTHPASTE CONTAINING SOLUBLE PYROPHOSPHATE SALTS

[75] Inventors: Todd W. Domke, Newtown, Pa.; Anthony E. Winston, East Brunswick, N.J.

[73] Assignee: Church & Dwight Co., Inc., Princeton, N.J.

[21] Appl. No.: 114,372

[22] Filed: Aug. 30, 1993

[51] Int. Cl.$^5$ .............................. A61K 9/16; A61K 9/18
[52] U.S. Cl. ........................................ 424/52; 424/49; 424/57
[58] Field of Search ...................... 424/49-58

[56] References Cited

U.S. PATENT DOCUMENTS

| | | | |
|---|---|---|---|
| 3,927,201 | 12/1975 | Baines et al. | 424/54 |
| 3,927,202 | 2/1975 | Harvey et al. | 424/57 |
| 3,937,321 | 2/1976 | Delaney et al. | 424/49 |
| 4,623,536 | 11/1986 | Winston et al. | 424/49 |
| 4,721,614 | 1/1988 | Winston et al. | 424/52 |
| 4,943,429 | 7/1990 | Winston et al. | 424/52 |
| 4,966,777 | 10/1990 | Gaffar et al. | 424/52 |
| 5,180,576 | 1/1993 | Winston et al. | 424/52 |
| 5,215,740 | 6/1993 | Domke et al. | 424/52 |

OTHER PUBLICATIONS

Chemical Abstracts, vol. 109, No. 8, The American Chemical Society, Aug. 22, 1988 "Title Page and p. 3".

Primary Examiner—Shep K. Rose
Attorney, Agent, or Firm—Charles B. Barris

[57] ABSTRACT

Toothpastes containing sodium bicarbonate and an alkali metal pyrophosphate salt dissolved in an aqueous sorbitol solution inhibit the formation of tartar. The toothpastes contain conventional ingredients such as thickeners, anti-caries agents, flavoring agents, and/or sweetening agents.

21 Claims, No Drawings

BAKING SODA TOOTHPASTE CONTAINING SOLUBLE PYROPHOSPHATE SALTS

FIELD OF THE INVENTION

The present invention relates to a toothpaste which contains baking soda and an alkali metal pyrophosphate salt.

BACKGROUND OF THE INVENTION

Calculus, or tartar as it is sometimes called, is the solid, hard mass of calcified material deposited on and adhering to the surfaces of the teeth. It is composed of inorganic salts which make the calculus hard and resistant to removal. Calculus is largely calcium phosphates, mainly hydroxyapatite with varying, but small, amounts of other inorganic salts.

Although not entirely understood, the general concept is that plaque, which is a sticky film of oral bacteria and their products, adheres to teeth and becomes calcified with the ultimate formation on the teeth of a hard mineral-like material consisting of calcium hydroxyapatite.

As the mature calculus develops, it becomes visibly white or yellowish in color unless stained or discolored by some extraneous agent. In addition to being unsightly and undesirable from an aesthetic standpoint, the mature calculus deposits can be constant sources of irritation to the gingiva. Further, the calculus can promote and retain plaque accumulations. Plaque is recognized as a prime etiological agent involved in gingivitis and periodontal disease. Additionally, plaque is porous and can retain toxic bacterial end products which are also associated with periodontal disease.

Methods for chemically reducing or preventing calculus formation have been directed at affecting the process at any of several stages in its development. One approach is to develop agents which inhibit the formation of the crystalline calcium phosphate or hydroxyapatite.

A wide variety of chemical and biological agents have been suggested to retard calculus formation or to remove calculus after it is formed. The chemical approach to calculus inhibition generally involves crystal growth inhibition which prevents the calculus from forming. Generally, once formed, mechanical removal by the dentist is necessary and is a routine dental office procedure.

The most widely used tartar control agents in dentrifices are sodium and potassium salts of pyrophosphoric acid. It is important that the pyrophosphate salt be in a readily available form so that the pyrophosphate ions $(P_2O_7^{-4})$ contact the enamel surfaces during use. The bioavailability of the ion is determined by the solubility of the salt both in the liquid vehicle of the dentrifice and in the water/expectorant mixture in which the dentrifice is dispersed during brushing of the teeth.

In a dentrifice containing sodium bicarbonate, i.e., baking soda, and the alkali metal salts of pyrophosphoric acid, the solubility of the pyrophosphate salt within the liquid vehicle of the dentrifice is greatly reduced. This suppression of solubility is due to the excess of sodium ions placed in solution by the sodium bicarbonate.

Therefore, there is a need to improve the solubility of alkali metal pyrophosphate salts within a baking soda tooth paste.

SUMMARY OF THE INVENTION

The present invention provides a dentrifice in the form of a toothpaste. The toothpaste comprises sodium bicarbonate, typically about 8-65%, preferably about 20-55%, most preferably 40-50%; an affective amount of an alkali metal pyrophosphate salt as an anti-tartar agent; and an aqueous solution of sorbitol in an amount sufficient to dissolve at least about 50% of the pyrophosphate salt and to provide the desired consistency to the toothpaste, typically at least about 30-70%, preferably about 40-60%. The pyrophosphate ion is more readily available because tetrasodium pyrophosphate is more soluble in the aqueous sorbitol solution used herein as the liquid vehicle than in the conventional aqueous liquid vehicles used in most toothpastes.

In a toothpaste, water is typically a desirable component. However, in the present toothpaste, water is not especially desirable and any additional water (i.e., water over and above that in the sorbitol solution), comprises only up to about 30%, preferably only up to 7% of the composition. The sorbitol solution is the main liquid vehicle. The water used to dissolve the sorbitol is that amount which is effective to solubilize it. Typically, the sorbitol solution is a 70% aqueous solution.

Optional, but preferred, components which are included in the dentrifices are organic thickeners and/or inorganic thickeners, surfactants, flavoring agents and/or sweetening agents, coloring agents and/or pigments, an anti-caries agent such as a soluble fluoride source, buffering agents such as alkali metal orthophosphates, phosphoric acid, alkali metal glycerophosphates, tartrates and citrates, and like components conventionally added to toothpastes. If desired, a secondary anti-calculus agent can be included.

The present invention further provides a method of preventing tartar formation on dental enamel which comprises contacting the enamel surface in the mouth with a toothpaste comprising sodium bicarbonate, an alkali metal pyrophosphate salt, and an aqueous sorbitol solution, with the amount of pyrophosphate salt dissolved in the toothpaste being sufficient to provide about 0.5-4.0% pyrophosphate ions.

DESCRIPTION OF THE PREFERRED EMBODIMENTS

Suitable pyrophosphate salts which may be incorporated in the toothpastes of the present invention include mono-, di-, tri- or tetra-alkali metal pyrophosphates and mixtures thereof. The preferred pyrophosphate salts include disodium pyrophosphate ($Na_2H_2P_2O_7$), tetrasodium pyrophosphate ($Na_4P_2O_7$), tetrapotassium pyrophosphate ($K_4P_2O_7$), and mixtures thereof. The pyrophosphates may be employed in their anhydrous as well as their hydrated forms. The levels of each these salts used are as follows (all are in the unhydrated form: $Na_2H_2P_2O_7$—about 1-10%, preferably about 1-5%, $Na_4P_2O_7$—up to about 2%, and $Na_4P_2O_7$—up to about 6%. Although a particular pyrophosphate salt, e.g., disodium or tetrapotassium pyrophosphate, may be the pyrophosphate initially added to the toothpaste, the actual pyrophosphate present in the toothpaste is dependent on both the final pH of the toothpaste and the salting-out effect of the sodium bicarbonate. Typically, the actual pyrophosphate is tetrasodium pyrophosphate. The quantity of dissolved pyrophosphate ion present in the toothpaste is dependent on the solubility in the presence of sodium bicarbonate, of the particular alkali metal pyrophosphate salt used, in the amount of aqueous sorbitol solution and in the added water, if present, as well as the final pH of the toothpaste.

The sodium bicarbonate particles may have a median particle size of about 5 to 200 microns, preferably about 10-150 microns, most preferably about 20-74 microns. The bicarbonate particles are incorporated in the toothpaste in varying amounts, depending upon the desired properties of the formulation. Higher levels of sodium bicarbonate, e.g., about 50-65%, allow it to be used as the sole abrasive. Such formulations remove plaque effectively, have a desirable low abrasivity, and provide an exceptionally clean feeling to the teeth and gums after brushing. Lower levels allow the incorporation of secondary abrasives. At very low levels, e.g., less than about 10%, the bicarbonate still enhances the clean feeling of the teeth and gums, but to a lesser degree than when high levels are used. It also provides effective buffering in the pH range of 7.5 to 9.5.

Suitable humectants for use herein include glycerin, propylene glycol, polypropylene glycol, and/or polyethylene glycol and other conventional humectants.

In addition to the above described required components, the toothpaste can contain a variety of conventionally used optional components.

Typically, the toothpastes contain a natural or synthetic organic thickener or gelling agent in amounts of up to about 2%, preferably about 0.1-2%. Suitable organic thickeners include sodium carboxymethyl cellulose, starch, gum tragacanth, carrageenan, xanthan gum, polyacrylate salts, polyvinylpyrrolidone, hydroxyethylpropyl cellulose, hydroxybutylmethyl cellulose, hydroxypropylmethyl cellulose, or hydroxyethyl cellulose, which are usually used in amounts of about 0.1-2.0%. Inorganic thickeners such as hydrated silicas may also be used in amounts of up to about 10% or greater.

Conventional abrasives or polishing materials are useful herein as a secondary abrasive provided they do not interfere with the solubility of the pyrophosphate ion. Suitable water-insoluble abrasives include sodium metaphosphate, potassium metaphosphate, calcium pyrophosphate, aluminum silicate, zirconium silicate, hydrated silica, hydrated alumina, bentonite, and/or the like. Preferred abrasive materials which may be admixed with the sodium bicarbonate include hydrated silica, silica gel, or colloidal silica and complex amorphous alkali metal aluminosilicates. Any of the foregoing water-insoluble abrasives may be present in amounts of up to about 40%, preferably in amounts up to about 20%, which amount will depend upon the amount of sodium bicarbonate used.

Organic surfactants are useful herein to achieve increased cleaning action, to assist thorough and complete dispersion of the anti-calculus agent throughout the oral cavity, and to improve the detergent and foaming properties of the toothpastes. Anionic, nonionic or ampholytic surfactants may be used, typically in amounts of about 0.1-3%

Examples of suitable anionic surfactants are the water-soluble salts of the higher alkyl sulfates such as sodium lauryl sulfate or other $C_8$-$C_{18}$ alkyl sulfates, water-soluble salts of higher fatty acid monoglyceride monosulfates such as the sodium salt of the monosulfate monoglyceride of hydrogenated coconut oil fatty acids, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds such as $C_{12}$-$C_{16}$ fatty acids, alkyl or acyl radicals, and the like. Examples of the last mentioned amides are N-lauroyl sarcosinate and the sodium, potassium, and ethanolamine salts of N-lauroyl, N-myristoyl, or N-palmitoyl sarcosinate which should be substantially free from soap or similar higher fatty acid materials.

Other suitable surfactants include non-ionic agents such as the condensates of sorbitan monostearate with ethylene oxide, the condensates of ethylene oxide with propylene oxide, or the condensates of propylene glycol (available under the trademark "Pluronics"). Other examples of water-soluble nonionic surfactants useful herein are the condensation products of ethylene oxide with various other compounds which are reactive therewith and have long hydrophobic chains (e.g., $C_{10}$-$C_{20}$ aliphatic chains) which condensation products ("ethoxamers") contain hydrophilic polyoxyethylene moieties, such as condensation products of polyethylene oxide with fatty acids, fatty alcohols, fatty amides, or polyhydric alcohols (e.g., sorbitan monostearate).

The various surfactants may be utilized alone or in admixture with one another. In toothpastes, the total amount used is preferably about 0.05%-5%, more preferably about 0.1%-2.0%.

When low levels of sodium bicarbonate are used, it is desirable to add an opacifying agent such as titanium dioxide in an amount of up to about 5%, preferably about 0.1-1%.

Sweetening agents are also useful herein. They include saccharin, sucralose, dextrose, levulose, aspartame, D-tryptophan, dihydrochalcones, acesulfame, sodium cyclamate, and calcium cyclamate. They are generally used in amounts of up to about 2%. Also useful as sweetening agents are xylitol and mannitol in amounts up to about 3% and 5%, respectively.

Anti-microbial agents can be included in the toothpastes to help inhibit plaque formation and gingivitis or to reduce mouth odor. For example, cationic antimicrobial agents such as cetyl pyridinium chloride or benzothonium chloride can be used. Bis-biguanides are also effective. Such agents include chlorhexidine (1,6-bis [$N^5$-p-chlorophenyl-N-biguanido]hexane), and the soluble and insoluble salts thereof and related materials such as 1,2-bis($N^5$-p-trifluoromethylphenyl-$N^1$-biguanido)ethane which are described more fully in U.S. Pat. No. 3,937,807 (issued Feb. 10, 1976 to Haefale), Belgian Pat. No. 843,244 (published Dec. 22, 1976) and Belgian Pat. No. 844,764 (published Jan. 31, 1977). If present, the secondary anti-microbials generally comprise about 0.01-0.5% of the composition. When using cationic agents, it is generally necessary to avoid using anionic surfactants in the formulation. Nonionic anti-microbials such as triclosan can be used. These materials have the advantage of not losing efficacy in the presence of anionic surfactants.

Soluble complex phosphate salts other than the pyrophosphate may be used as secondary anti-calculus agents, e.g., tripolyphosphates and hexametaphosphates.

The tooth gels can include a water-soluble fluoride ion source which is effective both as a pyrophosphatase inhibitor and as an anti-caries agent. Suitable fluoride ion sources include inorganic fluoride salts such as soluble alkali metal or alkaline earth metal salts, e.g., sodium fluoride, potassium fluoride, sodium fluorosilicate, ammonium fluorosilicate, sodium fluorozirconate and sodium monofluorophosphate. Alkali metal fluorides such as sodium fluoride, sodium monofluorophosphate, and mixtures thereof are preferred. The amount of the soluble fluoride ion source in the dentifrice is dependent on the particular compounds used and the type of dentrifice, but it must be incorporated in an effective, but nontoxic amount, generally up to about 5.0%. Any suitable minimum amount of fluoride may be used, but it is preferable to employ a quantity sufficient to release about 50 to 3500 ppm, preferably about 850–1500 ppm, of fluoride ions. In the case of sodium fluoride, the fluoride ion source is present in an amount from 0.05–0.65% preferably about 0.18–0.35%. In the case of sodium monofluorophosphate, the amount is about 0.2–2%, more typically about 0.65%–1.20%.

Various other materials may be incorporated in the toothpastes. Examples thereof are coloring and whitening agents, preservatives, silicones, and/or chlorophyll compounds. These adjuvants are incorporated in the toothpastes in amounts which do not substantially adversely affect the properties and characteristics desired and are selected and used in effective amounts, depending upon the particular adjuvant and type of toothpaste involved.

The pH of the toothpastes herein range from 7.0 to 10.0, preferably from 7.5 to 9.0. The pH is preferably achieved through a proper balancing of the bicarbonate and other additives.

The toothpastes herein are made using conventional mixing techniques and used in a conventional manner.

The following examples further illustrate the present invention, but it is understood that the invention is not limited thereto. All amounts and proportions referred to herein and in the appended claims are by weight and temperatures are in degrees Celsius unless otherwise indicated.

EXAMPLE 1

The following toothpaste containing about 1.3% pyrophosphate all in solution was prepared.

| | |
|---|---:|
| Sodium bicarbonate (mean particle size < 35) | 43.374 |
| Tetrasodium pyrophosphate | 2.000 |
| Sodium fluoride | 0.243 |
| Sorbitol (70% aqueous solution) | 40.100 |
| Glycerin | 4.104 |
| Polyethylene glycol (PEG-8) | 1.000 |
| Sodium carboxymethyl cellulose (9M31F) | 0.700 |
| Distilled water | 5.279 |
| Sodium saccharin | 1.000 |
| Sodium lauryl sulfate | 0.300 |
| Sodium lauroyl sarcosinate (30% solution) | 1.000 |
| Flavor | 0.900 |
| Total | 100.000 |

| | 2 | 3 | 4 | 5 |
|---|---:|---:|---:|---:|
| Sodium bicarbonate | 42.287 | 55.000 | 8.000 | 20.000 |
| Tetrasodium pyrophosphate | 2.000 | 2.000 | 6.000 | 4.000 |
| Tetrapotassium pyrophosphate | 0.000 | 0.000 | 0.000 | 3.000 |
| Hydrated silica abrasive | 0.000 | 0.000 | 0.000 | 4.300 |
| Thickening silica | 0.000 | 0.000 | 0.000 | 3.000 |
| Titanium dioxide | 0.000 | 0.000 | 0.000 | 0.200 |
| Calcium pyrophosphate | 0.000 | 0.000 | 8.000 | 0.000 |
| Sodium fluoride | 0.243 | 0.243 | 0.243 | 0.243 |
| Sorbitol (70% solution) | 40.100 | 40.100 | 40.100 | 40.100 |
| Glycerin | 5.000 | 5.000 | 5.000 | 5.000 |
| Polyethylene glycol (PEG-8) | 0.000 | 0.000 | 1.000 | 1.000 |
| Sodium carboxymethyl cellulose | 0.600 | 0.600 | 0.600 | 0.600 |
| Distilled water | 6.000 | 5.279 | 5.279 | 10.000 |
| Sodium saccharin | 0.650 | 0.650 | 0.650 | 0.650 |
| Sodium lauryl sulfate | 0.500 | 0.500 | 0.500 | 0.500 |
| Sodium lauroyl sarcosinate (30% solution) | 1.670 | 1.670 | 1.670 | 1.670 |
| Flavor | 0.950 | 0.950 | 0.950 | 0.950 |
| TOTAL | 100.000 | 100.000 | 100.000 | 100.000 |
| Approximate % of pyrophosphate which is in solution | 80% | 50% | 75% | 55% |

| | 6 | 7 | 8 | 9 |
|---|---:|---:|---:|---:|
| Sodium bicarbonate | 35.000 | 43.220 | 14.979 | 65.000 |
| Tetrasodium pyrophosphate | 0.000 | 0.000 | 2.500 | 2.000 |
| Tetrapotassium pyrophosphate | 3.400 | 5.000 | 0.000 | 0.000 |
| Disodium dihydrogen pyrophosphate | 0.000 | 0.200 | 0.000 | 0.000 |
| Hydrated silica abrasive | 5.500 | 0.000 | 5.000 | 0.000 |
| Thickening silica | 0.000 | 0.000 | 5.000 | 0.000 |
| Titanium dioxide | 0.100 | 0.000 | 0.500 | 0.000 |
| Sodium fluoride | 0.243 | 0.000 | 0.221 | 0.243 |
| Sodium monofluorophosphate | 0.000 | 0.780 | 0.000 | 0.000 |
| Sorbitol (70% solution) | 44.657 | 40.100 | 35.000 | 24.327 |
| Xylitol | 3.000 | 0.000 | 0.000 | 0.000 |
| Mannitol | 0.000 | 0.000 | 5.000 | 0.000 |
| Glycerin | 4.000 | 0.000 | 4.000 | 4.000 |
| Polyethylene glycol (PEG-8) | 1.000 | 1.000 | 0.000 | 1.000 |
| Sodium carboxymethyl cellulose | 0.300 | 0.600 | 0.800 | 0.300 |
| Distilled water | 0.000 | 6.000 | 25.000 | 0.000 |
| Sodium saccharin | 0.650 | 0.700 | 0.500 | 0.800 |
| Sodium lauryl sulfate | 1.200 | 0.300 | 0.800 | 0.330 |
| Sodium lauroyl sarcosinate (30% solution) | 0.000 | 1.000 | 0.000 | 1.000 |
| Flavor | 0.950 | 1.100 | 0.700 | 1.000 |
| TOTAL | 100.000 | 100.000 | 100.000 | 100.000 |
| Approximate % of pyrophosphate which is in solution | 100% | 70% | 80% | 75% |

EXAMPLE 10

This example shows the effect of sodium bicarbonate (NaHCO$_3$) on the solubility of tetrasodium pyrophosphate.

| | Wt % of P$_2$O$_7^{-4}$ in Solution | |
|---|---:|---:|
| | Without NaHCO$_3$ | With Saturated NaHCO$_3$ |
| Distilled Water | 4.03 | 1.77 |
| Glycerin | 0.04 | 0.12 |
| 70% Aqueous Sorbitol Solution | 5.97 | 4.18 |
| 18% Aqueous Mannitol Solution | — | 2.09 |
| 60% Aqueous Xylitol Solution | — | 2.44 |

The results show that, in the presence of sufficient sodium bicarbonate to saturate the water, the solubility of the pyrophosphate ion ($P_2O_7^{-4}$) was suppressed from 4.03% to 1.77%. The results show that, in the absence of sodium bicarbonate, the pyrophosphate is more soluble in the 70% aqueous sorbitol solution than it is in the distilled water. While the presence of the bicarbonate in the aqueous sorbitol solution also suppressed the pyrophosphate solubility, the decrease was not as great as that observed with water. The pyrophosphate was not soluble in glycerin in either case. The results further show that other similar polyols, i.e., mannitol and xylitol, were not as effective as sorbitol, in increasing pyrophosphate solubility in the presence of bicarbonate.

EXAMPLE 11

This example shows the solubility of tetrasodium pyrophosphate in various dentrifice solvent systems saturated with sodium bicarbonate. The percent solubility of the pyrophosphate ion ($P_2O_7^{-4}$) is given as weight %.

| Water* | Glycerin* | 70% Sorbitol Solution | Wt % $P_2O_7^{-4}$ |
|---|---|---|---|
| 1 | 0 | 0 | 1.77 |
| 0 | 1 | 0 | 0.12 |
| 0 | 0 | 1 | 4.18 |
| ½ | ½ | 0 | 0.44 |
| ½ | 0 | ½ | 2.19 |
| 0 | ½ | ½ | 1.73 |
| ⅓ | ⅓ | ⅓ | 1.01 |
| ⅔ | 1/6 | 1/6 | 1.15 |
| 1/6 | ⅔ | 1/6 | 1.48 |
| 1/6 | 1/6 | ⅔ | 2.08 |

*Weight fraction of solvent system

The results show that the best solubility (4.18%) was in the 70% aqueous sorbitol solution and the worst solubilities were in solvent systems containing no aqueous sorbitol solution (0.12% for glycerin and 0.44% for a glycerin/water mixture).

In addition to the levels and combinations of ingredients shown in these examples, others can be used which are consistent with the invention disclosed and claimed herein.

What is claimed is:

1. A toothpaste consisting essentially of:
   a. about 10-65% sodium bicarbonate;
   b. an alkali metal pyrophosphate salt present in an amount which is effective as an anti-tartar agent, of which amount at least 50% is dissolved in the toothpaste; and
   c. an aqueous solution of sorbitol, as a main liquid vehicle, in an amount which is sufficient to dissolve at least about 50% of the amount of the alkali metal pyrophosphate salt added and to provide the desired consistency to the toothpaste.

2. The toothpaste of claim 1, wherein the sodium bicarbonate is about 20-55%; wherein the pyrophosphate salt added is selected from the group consisting of tetrasodium pyrophosphate, disodium dihydrogen pyrophosphate, tetrapotassium pyrophosphate, and mixtures thereof; and wherein the aqueous sorbitol solution is about 70% aqueous.

3. The toothpaste of claim 2, wherein the sodium bicarbonate is about 40-50%; wherein the pyrophosphate salt added is tetrasodium pyrophosphate present in an amount of about 1-10%; and wherein the about 70% aqueous solution of sorbitol is about 30-70% of the toothpaste.

4. The toothpaste of claim 3, wherein the about 70% aqueous; solution of sorbitol is about 40-60% and wherein the pyrophosphate salt added is tetrasodium pyrophosphate in an amount of about 1-5%.

5. The toothpaste of claim 2, wherein the sodium bicarbonate is about 40-50%; wherein the pyrophosphate salt added is disodium dihydrogen pyrophosphate in an effective amount of about 1-10%; and wherein the about 70% aqueous solution of sorbitol present is about 30-70% of the toothpaste.

6. The toothpaste of claim 2, wherein the sodium bicarbonate is about 40-50%; wherein the pyrophosphate salt added is tetrapotassium pyrophosphate in an amount of up to about 6%; and wherein the about 70% aqueous solution of sorbitol is about 30-70% of the toothpaste.

7. The toothpaste of claim 4, wherein the amount of pyrophosphate ions present in the toothpaste is about 0.5-2%.

8. The toothpaste of claim 1, wherein the median particle size of the sodium bicarbonate is about 5-200 microns.

9. The toothpaste of claim 8, wherein the median particle size of the sodium bicarbonate is about 10-150 microns.

10. The toothpaste of claim 8, wherein the median particle size of the sodium bicarbonate is about 20-74 microns.

11. The toothpaste of claim 1, wherein the amount of the surfactant is about 0.1-3%; and wherein the amount of the flavoring agent is about 0.05-2%;.

12. The toothpaste of claim 1, further consisting essentially of: water, a water-insoluble abrasive, a humectant, an opacifying agent, an inorganic thickening agent, a surfactant, and a sweetening agent; and wherein the water is present in an effective amount of up to about 6%; wherein the water-insoluble abrasive is calcium pyrophosphate present in an effective amount of up to about 8% or hydrated silica present in an effective amount of up to about 5.5%; wherein the humectant is polyethylene glycol present in an effective amount of up to about 2%; wherein the opacifying agent is titanium dioxide; wherein the inorganic thickening agent is silica present in an effective amount of up to about 5%; wherein the surfactant is sodium lauryl sulfate present in an amount of about 0.3-1.4% and sodium lauroyl sarcosinate (30%) present in an amount of about 1.7%; and wherein the sweetening agent is sodium saccharin present in an amount of about 0.5-0.8%, xylitol present in an effective amount of up to about 3%, or mannitol present in an effective amount of up to about 5%.

13. A toothpaste consisting essentially of:
   a. about 10-65% sodium bicarbonate;
   b. an alkali metal pyrophosphate salt present in an amount which is sufficient to provide about 0.5-5% by weight of dissolved pyrophosphate ions; and
   c. an aqueous solution of sorbitol, as a main liquid vehicle, in an amount which is sufficient to dissolve at least 50% of the pyrophosphate salt added and to provide the desired consistency to the toothpaste.

14. The toothpaste of claim 13, wherein the sodium bicarbonate has a median particle size of about 5-200 microns.

15. The toothpaste of claim 12, wherein the sodium bicarbonate is present in an amount of about 20-55%;

wherein the pyrophosphate salt added is tetrasodium pyrophosphate present in an amount of about 1–10%; and wherein the aqueous sorbitol solution is an about 70% solution present in an amount of about 30–70% of the toothpaste.

16. The toothpaste of claim 13, wherein the sodium bicarbonate is present in an amount of about 40–45%; wherein the tetrasodium pyrophosphate is about 1–5%; wherein the about 70% aqueous sorbitol solution is about 40–52%; and wherein the balance, if any, is selected from the group consisting of a humectant, added water, a thickener, a fluoride source, a surfactant, a sweetening agent, or a flavoring agent.

17. An improved sodium bicarbonate-based toothpaste which consists essentially of about 10–65% sodium bicarbonate, an alkali metal pyrophosphate salt, and an aqueous vehicle, wherein the improvement is the addition, as the main aqueous vehicle, of an aqueous solution of sorbitol in an amount which is sufficient to dissolve at least about 50% of the amount of the alkali metal pyrophosphate salt added.

18. A method of improving the solubility of a pyrophosphate salt in a toothpaste which consists essentially of 10–65% by weight of sodium bicarbonate, a liquid vehicle, and the pyrophosphate salt, which comprises the step of adding to the toothpaste, as the main liquid vehicle, an aqueous solution of sorbitol in an amount sufficient to dissolve about 50% of the pyrophosphate salt.

19. The method of claim 18, wherein the aqueous solution of sorbitol is a 70% aqueous solution.

20. The method of claim 18, wherein the amount of dissolved pyrophosphate is about 0.5–5% by weight.

21. The method of claim 20, wherein the 70% aqueous solution of sorbitol is the sole liquid vehicle.

* * * * *